United States Patent [19]

Trick

[11] Patent Number: 4,574,792
[45] Date of Patent: Mar. 11, 1986

[54] PENILE ERECTILE SYSTEM

[75] Inventor: Robert E. Trick, Racine, Wis.

[73] Assignee: Medical Engineering Corporation, Racine, Wis.

[21] Appl. No.: 624,624

[22] Filed: Jun. 26, 1984

Related U.S. Application Data

[63] Continuation-in-part of Ser. No. 305,048, Sep. 24, 1981, Pat. No. 4,369,771, and a continuation-in-part of Ser. No. 426,566, Sep. 29, 1982, Pat. No. 4,457,335.

[51] Int. Cl.⁴ ............................................. A61F 5/00
[52] U.S. Cl. ......................................... 128/79; 623/11
[58] Field of Search .................................. 128/79; 3/1

[56] References Cited

U.S. PATENT DOCUMENTS

| | | | |
|---|---|---|---|
| 3,758,073 | 9/1973 | Schulte | 251/342 |
| 3,954,102 | 5/1976 | Buuck | 128/79 |
| 4,353,360 | 10/1982 | Finney et al. | 128/79 |
| 4,364,379 | 12/1982 | Finney | 128/79 |
| 4,369,771 | 1/1983 | Trick | 128/79 |
| 4,383,525 | 5/1983 | Scott et al. | 128/79 |
| 4,407,278 | 10/1983 | Burton et al. | 128/79 |
| 4,449,520 | 5/1984 | Palomar et al. | 128/79 |

Primary Examiner—Paul J. Hirsch
Attorney, Agent, or Firm—Quarles & Brady

[57] ABSTRACT

A self-contained penile implant includes a pressure chamber, a fluid reservoir, a pump for transferring fluid from the reservoir to the pressure chamber and a release valve which can be manually deformed to release the pressure in the pressure chamber and permit fluid to flow from the pressure chamber to the reservoir.

6 Claims, 7 Drawing Figures

PENILE ERECTILE SYSTEM

RELATED APPLICATIONS

This is a continuation in part of my earlier application Ser. No. 305,048 filed Sept. 24, 1981, now U.S. Pat. No. 4,369,771 and Ser. No. 426,566 filed Sept. 29, 1982, now U.S. Pat. No. 4,457,335.

FIELD OF THE INVENTION

The present invention relates to a penile erectile system. More particularly, it relates to an inflatable, self-contained implantable penile erectile system.

DESCRIPTION OF THE PRIOR ART

There are some cases of erectile impotence for which the surgical implantation of a penile erectile system is the only practical means of remedying the impotency. In such cases in the past, several different types of implantable penile erectile systems have been employed.

One type of implantable penile erectile system which has been employed is an inflatable system which includes two inflatable and distensible tubes each of which is surgically implanted in a separate corporus cavernosum of the penis. Each of the tubes is connected by tubing to a relatively large reservoir of inflating and pressurizing fluid which is implated elsewhere in the body necessitating additional abdominal surgery. An erection is achieved by inflating and pressurizing the distensible tubes. The device of U.S. Pat. No. 4,009,711 is representative of this type of system.

Another type of penile erectile system comprises a pair of rods of suitable stiffness which are surgically implanted into the corpora cavernosa of the penis. A significant advantage of this system is that the amount of surgery involved is minimal as there is no pressure bulb or tubing to implant. A disadvantage of this system is that the permanent stiffness of the rods can be a source of physical pain and embarrassment to the patient. Representative penile erectile systems employing rod implants are disclosed in U.S. Pat. No. 3,893,476 and U.S. Pat. No. 4,066,037.

Another implantable erectile system which combines some of the features of both the inflatable system and the rod implant system is disclosed in U.S. Pat. No. 4,201,202. The system disclosed therein includes a rod within a sleeve positioned about the rod to form a chamber. An erection is achieved by pressurizing the chamber to straighten and support the rod and the chamber is depressurized by use of a pressure control valve.

Still another implantable erectile system is that shown in U.S. Pat. No. 4,399,811. The system disclosed consists of two identical, self-contained pressurizable implants which can be surgically implanted completely within the penis. The implants have a pump in the tip and a pressure control valve at the base. The surgery involved is minimal and similar to that required for a rod type implant system.

SUMMARY OF THE INVENTION

It is the general object of the present invention to disclose a penile erectile system consisting of a pair of implantable, self-contained pressurizable penile implants, each of which includes a reliable, improved pump and release valve. The implants can be surgically implanted completely within the penis as easily as implanting a rod type implant.

The implants of the penile erectile system of the present invention contain a pressure chamber, a fluid reservoir, a pump for transferring fluid from the reservoir to the pressure chamber to make it rigid and a release valve having a manually deformable housing. When the housing is deformed the release valve opens and the pressure chamber is depressurized.

The preferred implants of the penile erectile system of the present invention each have an elongated body having a relatively short, proximal stem portion, a distal tip portion, and an elongated flexible intermediate portion containing a pair of concentric cylindrical chambers. Both of the chambers are substantially filled with hydraulic fluid. The body of the implant also contains an integral pump means for transferring fluid under pressure from the outer chamber to pressurize the non-distensible inner pressure chamber and a release valve which has a housing which can be manually deformed to depressurize or deflate the pressure chamber.

The penile erectile system of the present invention, in addition to being compact and thus minimizing the amount of surgery required, also has the advantage of having a minimum number of fluid connections, thus reducing the risk of leakage.

The foregoing and other objects and advantages will become apparent from the description which follows:

DESCRIPTION OF THE PREFERRED EMBODIMENT

Figure 1:
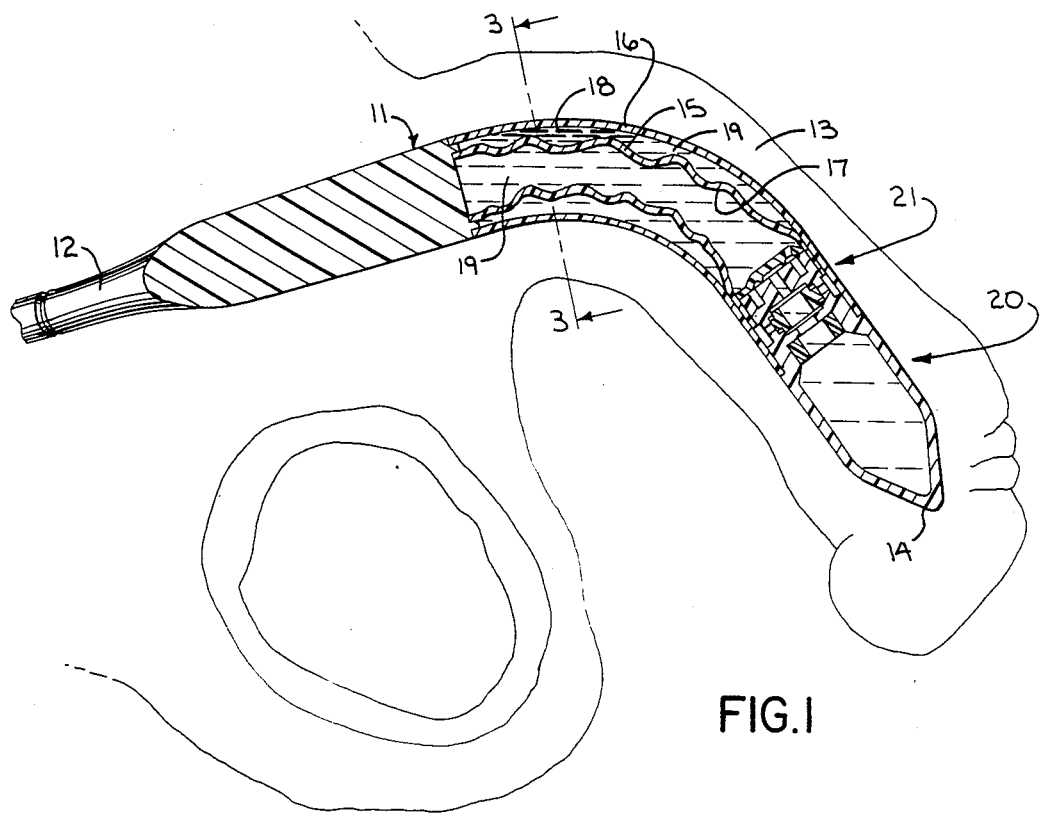
FIG. 1 is a side view, partly in section, of the preferred embodiment of the penile erectile system of the present invention showing one of the two identical penile implants surgically implanted in a male and in a nonpressurized condition.

The preferred embodiment of the penile erectile system of the present invention, which is shown in the drawings, comprises a pair of elongated penile implants 11, 11'. The two implants 11, 11' are identical, therefore, only one will be described in detail.

Figure 2:
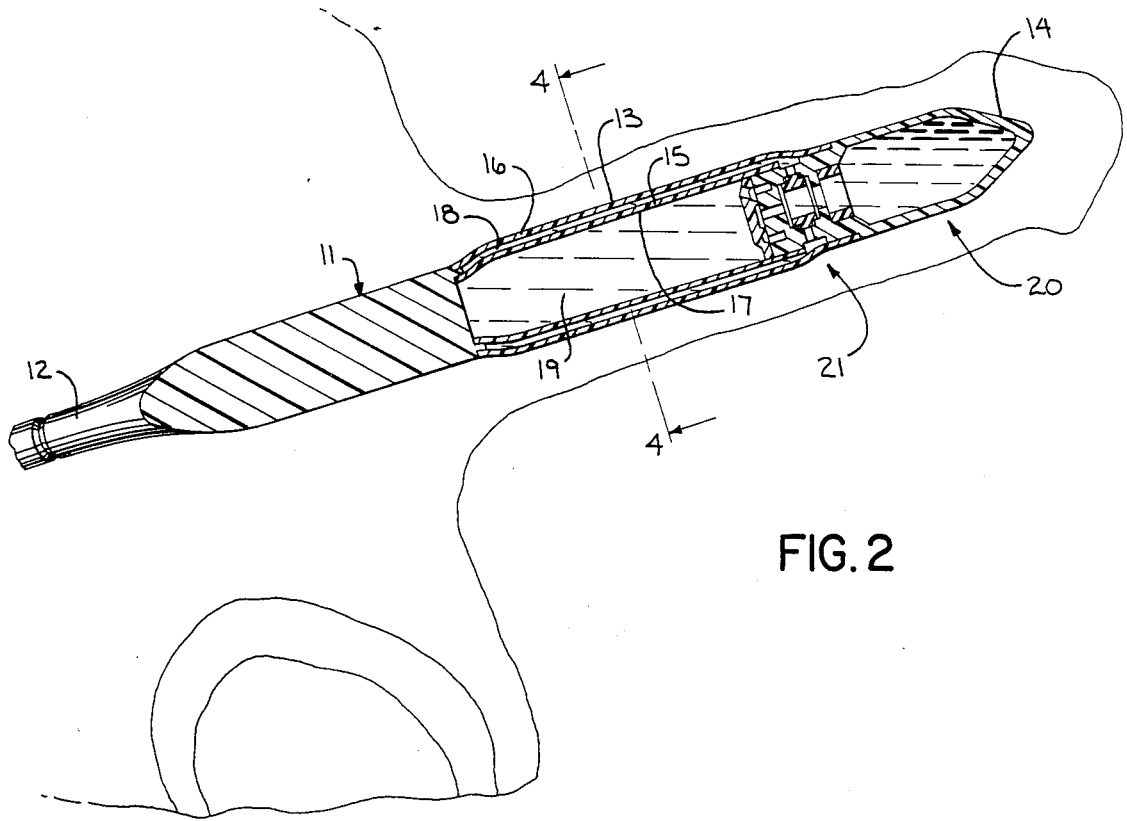
FIG. 2 is a side view similar to FIG. 1, except that the implant is pressurized.
Figure 3:
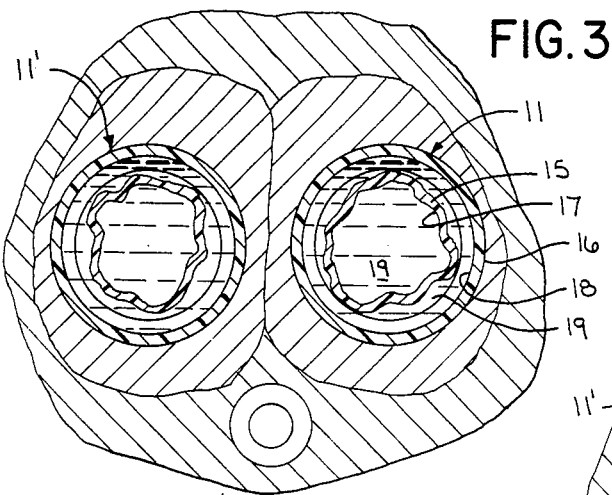
FIG. 3 is an enlarged cross sectional view taken along the line 3—3 in FIG. 1.
Figure 4:
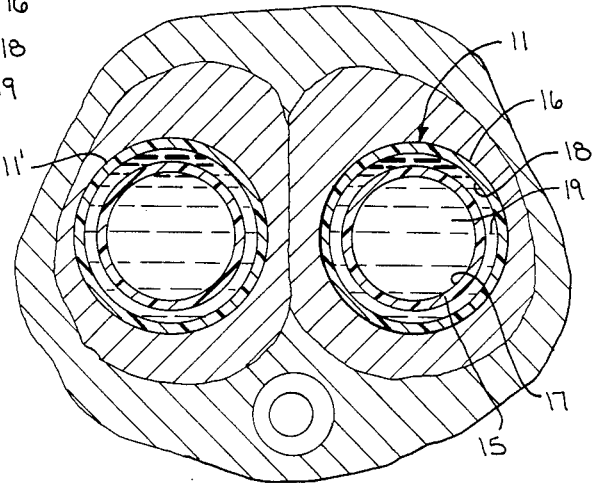
FIG. 4 is an enlarged cross sectional view taken along the line 4—4 in FIG. 2.

As seen best in FIGS. 1 and 2, the implant 11 has a proximal stem 12, and intermediate cylindrical portion 13, and a distal tip 14. The stem portion 12 which is of a relatively stiff material is implanted in the root end of a corpus cavernosum and the intermediate cylindrical portion 13 and the hollow tip portion 14 which are relatively flexible are implanted in the portion of the corpus cavernosum in the pendulous penis. As seen in FIGS. 3 and 4, each of the implants 11, 11' is positioned in a separate corpus cavernosum of the penis.

The intermediate cylindrical portion 13 of the implant 11 preferably includes a pair of flexible, collapsible concentric cylindrical sleeves 15 and 16 which are attached in a fluid tight manner to the stem 12 and to the tip 14 to form a pair of concentric chambers 17 and 18, respectively. The sleeve 15 which forms the wall of the inner or pressure chamber 17 is of a relatively inelastic material, such as a silicone coated mesh or woven fabric, so that the chamber 17 is non-distensible even when pressurized. The sleeve 15 cooperates with the sleeve 16 which is spaced outwardly from the sleeve 15 to form the outer chamber 18 which serves as a fluid reservoir. The sleeve 16 may be made of a distensible material such as noreinforced silicone rubber. The necessary fluid tight seals between the sleeves 15 and 16 and the stem portion 12 and tip portion 14 may be made with a suitable adhesive or by other suitable means.

As seen in FIGS. 1 and 3, when the implant 11 is in a non-pressurized state both the chambers 17 and 18 are substantially filled with a non-compressible biocompatible hydraulic fluid 19, such as saline or a free flowing silicone gel. In the non-pressurized state, the flexible, intermediate cylindrical portion 13 of the implant 11 flexes and permits the penis to assume a substantially normal, flaccid position as seen in FIG. 1. However, when the implant 11 is in the pressurized state, as seen in FIGS. 2 and 4, the intermediate cylindrical portion 13 is rigid as the result of the non-distensible pressure chamber 17 being completely filled with fluid under pressure and the penis assumes an erectile position.

The integral pump 20 and release valve 21 for pressurizing the inner chamber 17 and relieving the pressure in chamber 17, respectively, will now be described in connection with FIGS. 5, 6 and 7.

Figure 5:
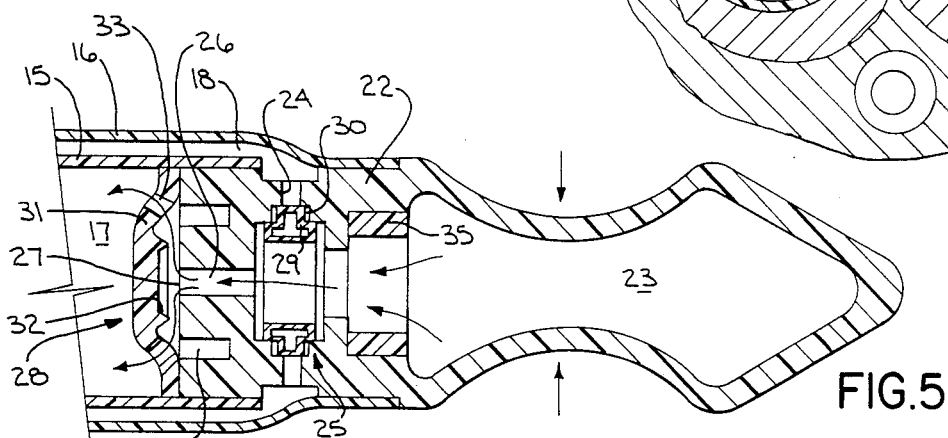
FIG. 5 is an enlarged view, partly in section, of the tip portion of the implant of FIG. 1 showing the positions of the pump and release valve components when the pump is being squeezed to pressurize the inner chamber.
Figure 6:
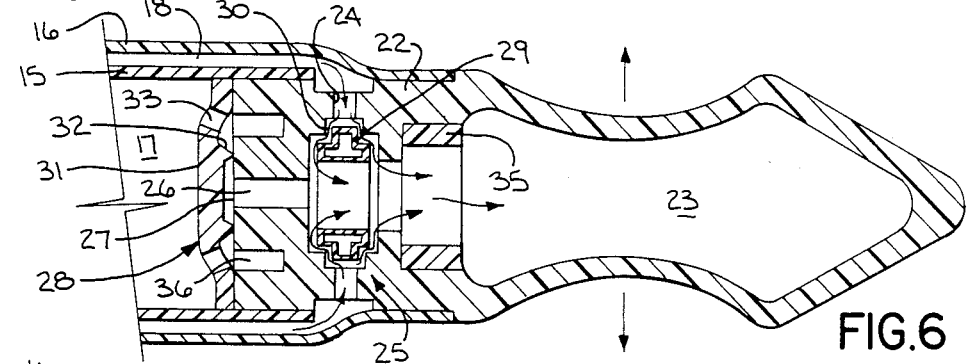
FIG. 6 is an enlarged view similar to FIG. 5 showing the positions of the pump and valve components when the squeezing force is removed.
Figure 7:
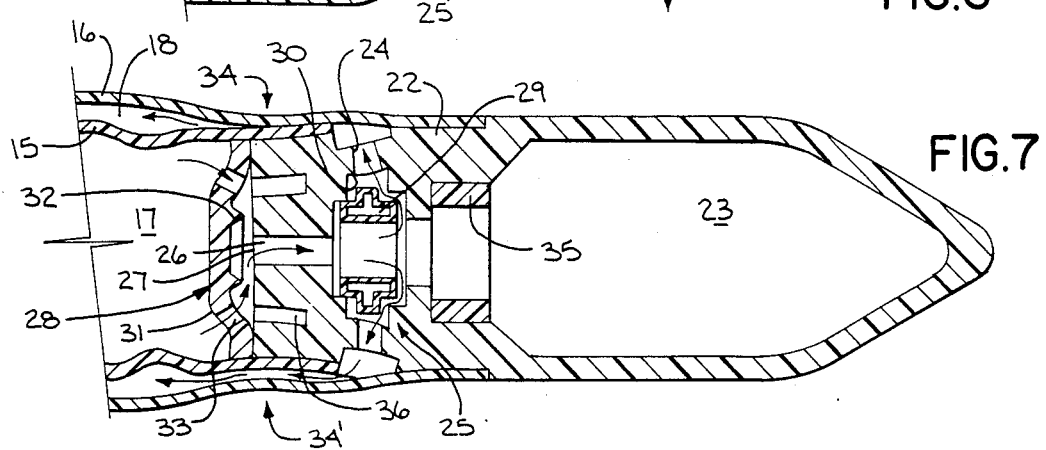
FIG. 7 is a view similar to FIGS. 5 and 6 showing the positions of the pump and valve components when the release valve housing is manually deformed to open the valve.

As seen in FIGS. 5, 6, and 7, a valve housing 22 separates the chambers 17 and 18 from a pumping chamber 23 in the tip 14. An inlet passage 24 in the housing 22 leads from the outer chamber 18 to the pumping chamber 23. An inlet valve 25 controls the flow of fluid 19 from chamber 18 to pumping chamber 23. An outlet passage 26 in the housing 22 leads from the pumping chamber 23 to the pressure chamber 17. The exit 27 of the passage 26 which leads to the chamber 17 is normally closed by an outlet valve 28.

As seen in FIG. 5, when the pumping chamber 23 is squeezed the passage 24 is closed by the inlet valve 25 which consists of a deformable, preferably hollow, ring 29 which flattens and seats against an annular groove 30 in the housing 22. When the fluid pressure in the reservoir 18 exceeds that in the pumping chamber 23 the ring 29 is pulled off its seat as seen in FIG. 6.

Still referring to FIG. 6, it can be seen that the outlet valve 28 includes a diaphragm 31 which closes the exit 27 of the passage 26. The diaphragm 31 has an outwardly projecting annular ring seal 32 which encloses an imperforate central portion and forms a seal with that protion of the housing 22 which surrounds the exit 27 when the pressure in the pressure chamber 17 exceeds that in the pumping chamber 23. When the resilient wall of the pumping chamber 23 is squeezed as shown in FIG. 5 the fluid pressure in the pumping chamber 23 exceeds that in pressure chamber 17 and the ring seal 32 is moved out of sealing engagement with the housing 22 allowing fluid to flow from the pumping chamber and passage 26 through openings 33 in the area of the diaphragm 31 outside the ring seal 32 and into pressure chamber 17. Although only two openings 33 are shown, the diaphragm 31 will usually have four on more such openings.

The implant 11 is pressurized by sequentially squeezing the pumping chamber 23 to force the fluid 19 from the pumping chamber 23 into nondistensible pressure chamber 17 under pressure. When the pumping chamber is first squeezed the fluid 19 originally in the pumping chamber 22 is forced through the passage 26 into the pressure chamber 17 in the manner described and shown by the arrows in FIG. 5. The increased pressure in the pumping chamber 23 flattens the hollow ring 29 against its seat in the groove 30 closing passage 24 and preventing fluid from flowing into reservoir chamber 18.

When the squeezing force is removed, a reduced pressur is formed in the pumping chamber 23 and as a result the hollow ring 29 is sucked off its seat in the groove 30 allowing fluid 19 to flow from chamber 18 into the pumping chamber 23 as shown by the arrows in FIG. 6.

When the pressure chamber 17 is sufficiently pressurized and rigid, the pumping action is stopped whereby the exit of the passage 26 is closed by pressure of the fluid 19 in pressure chamber 17 upon the backside of the diaphragm 31 which causes the annular ring seal 32 to seat as seen in FIGS. 1, 3 and 6.

As seen in FIG. 7, the pressure chamber 17 is depressurized by manually squeezing and deforming the housing 22 at points 34, 34' so that leak paths exist about the inlet valve 25 and outlet valve 28. The leak paths are shown by arrows. The deformation of the housing 22 causes the diaphragm 31 to bow away from sealing engagement with the housing 22 so that a first leak path exists whereby fluid 19 can leave the pressure chamber 17. The deformation also causes the hollow ring 29 to be moved off its seat in the annular groove 31 so that a second leak path exists so that the fluid from the pressure chamber 17 can return to the reservoir 18.

In the preferred embodiment of the invention, there is a stiffening ring 35 which prevents the housing 22 from being deformed during pumping and an annular groove 36 in the housing 22 about the exit 26 which makes it easier to deform the housing 22 to establish the leak paths.

The non-distensible inner chamber 17 of the penile implant when pressurized provides the rigidity required to maintain the penis in an erectile position. Therefore, it must be of sufficient volume and size to perform this function. In contrast, the outer chamber 18 serves primarily as a reservoir of pressurizing fluid for the inner chamber and is sized accordingly. The exact dimensions of the inner and outer chambers are not critical as long as they are adequate to provide their desired function.

The sleeve 15 which forms the wall of the "non-distensible" chamber 17 must be relatively inelastic and is preferably made of a dacron mesh or fabric covered with silicone material that will not stretch when filled with fluid and pressurized. In contrast, the sleeve 16 may be either distensible or non-distensible. The diameters of the sleeves 15 and 16 can vary but are normally sized so that the implant in the non-pressurized state will fill the corpora cavernosa. It will be appreciated that the term non-distensible or inelastic is intended to cover any material which possesses the desired properties which enable it to provide its described function.

The term "substantially filled" as used herein to describe the fluid content of a chamber means that a chamber contains about 60% to about 95% or more of its capacity of a non-compressible fluid such as water, saline or a free flowing gel. The actual content of fluid can vary; however, the implant when "substantially filled" should be still sufficiently flexible so that the penis can assume a normal flaccid position.

The proximal stem portion 12 of the implant preferably has a Shore A hardness of about 70, the distal tip portion 12 a Shore A hardness of about 20, and each of the materials has sufficient tensile strength for its intended use. In the preferred embodiments of the drawings, the hollow tip is tapered and is made of a self-sealing silicone elastomer which allows fluid to be added to or removed from the implant with a fine hollow needle and a syringe.

The deformable housing 22 is formed of a resilient material such as silicone rubber or polyurethane having a suitable durometer e.g. Shore A 50. The stiffening ring 35 which prevents the inlet and outlet valves from being deformed during pumping is preferably made of stainless steel. The deformable ring 29 which may be hollow and tubular is of a soft elastomer and it expands radially slightly to form a seal with its groove when the pump is squeezed because it lacks structural rigidity. It is sucked or lifted off its seat when the pressure in the pumping chamber is less than in the reservoir.

All of the parts and components of the prosthesis are preferably made of or covered with medical grade silicone rubber which is non-reactive, non-toxic and well tolerated by the adjacent organic tissues. Silicone rubber is preferred because it is quite resistant to wear and remains functional for long periods of time. However, other suitable materials possessing desirable properties may also be employed.

The preferred method of implantation of the erectile system is through an incision made in the penis. After appropriate incision, each corpus cavernosum is dilated distally and proximally to accept the implants. The appropriate anatomical measurements are made to insure that the proximal stem of the implant or implants will be positioned at the base of the penis below the pelvic bone. An implant or implants having an appropriately sized intermediate section and distal tip is inserted into the corpus cavernosum of the penis. The distal tip is positioned in the glans end of the corpus cavernosum. The proximal stem of the implant then is anchored in the root end of the corpus cavernosum.

The identical procedure is performed on the other side of the penis to complete the surgical procedure. The proximal stems of the two implants preferably will diverge laterally to accommodate the anatomy, to provide lateral stability to the penis and to prevent rotation of the implants. The incision is then closed.

It is to be understood that the foregoing description has been for purposes of illustration and that a number of modifications and changes may be made without departing from the spirit and scope of the present invention. For example, although the implants described have solid stems for anchoring the implants, the stems could be hollow and contain a reservoir, if desired. In addition, although implants have been described and illustrated in which the pressure chamber is one of two concentric chambers and the outer chamber is a reservoir, other types of pressure chamber and reservoirs could be employed. It also should be understood that the pump and release valve of the present invention may be used in other medical devices.

I claim:

1. A penile implant comprising an elongated unitary body having a tip at one end, an anchoring stem at the other end, an intermediate portion having a pressure chamber, a reservoir for fluid for pressurizing the pressure chamber, and pump and valve means within the body for transferring fluid from the reservoir to the pressure chamber to pressurize it and make it rigid and for releasing the pressure in said pressure chamber, said pump and valve means comprising:
   (a) a pump having a pumping chamber;
   (b) a deformable valve housing positioned between and separating said pumping chamber from said pressure chamber and said reservoir;
   (c) an inlet passage in said housing leading from the reservoir to the pumping chamber;
   (d) an inlet valve controling flow through said inlet passage, said inlet valve opening when the pressure in the reservoir exceeds that in the pumping chamber or the housing is deformed;
   (e) an outlet passage in said housing leading from the pumping chamber to the pressure chamber; and
   (f) an outlet valve controlling flow through said outlet passage, said outlet passage being normally closed but opening when pressure in the pumping chamber exceeds that in the pressure chamber or the housing is deformed.

2. The implant of claim 1 in which the inlet valve comprises an annular groove in the housing and a deformable ring which seats in that groove when pressure in the pumping chamber exceeds that in the reservoir.

3. The implant of claim 1 in which the outlet valve is a diaphragm removably closing the exit of the outlet passage, said diaphragm having an imperforate central portion surrounded by a ring seal that seats about the exit of the outlet passage and prevents flow therethrough when the pressure in the pressure chamber exceeds that in the pumping chamber, said diaphragm having openings outside of the periphery of the ring seal through which fluid can flow when the diaphragm is moved out of seating relationship with the housing when pressure in the pumping chamber exceeds that in the pressure chamber or the valve housing is deformed.

4. The implant of claim 1 in which the reservoir and pressure chamber are concentric chambers and the pressure chamber is a non-distensible inner chamber.

5. The implant of claim 1 in which the valve housing includes a stiffening member adjacent the pumping chamber which prevents the valve housing from being deformed during pumping.

6. A valve for a medical device having a pressure chamber, a reservoir for pressurizing fluid and a pump; said valve comprising:
   (a) a deformable valve housing positioned between and separating said pump from said pressure chamber and said reservoir;
   (b) an inlet passage in said housing leading from the reservoir to the pump;
   (c) an inlet valve controlling flow through said inlet passage, said inlet valve opening when the pressure in the reservoir exceeds that from the pump or the housing is deformed;
   (d) an outlet passage in said housing leading from the pump to the pressure chamber; and
   (e) an outlet valve controlling flow through said outlet passage, said outlet passage being normally closed but opening when pressure from the pump exceeds that in the pressure chamber or the housing is deformed.

* * * * *